(12) United States Patent
Kiplinger et al.

(10) Patent No.: US 8,481,002 B2
(45) Date of Patent: Jul. 9, 2013

(54) METHOD OF PREPARATION OF URANIUM NITRIDE

(75) Inventors: Jaqueline Loetsch Kiplinger, Los Alamos, NM (US); Robert Kenneth James Thomson, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 189 days.

(21) Appl. No.: 13/010,588

(22) Filed: Jan. 20, 2011

(65) Prior Publication Data

US 2012/0073956 A1    Mar. 29, 2012

Related U.S. Application Data

(60) Provisional application No. 61/385,850, filed on Sep. 23, 2010.

(51) Int. Cl.
 *A61K 51/00* (2006.01)
 *A61M 36/14* (2006.01)
(52) U.S. Cl.
 CPC ................................... *A61K 51/00* (2013.01)
 USPC ........................................................ 424/1.11

(58) Field of Classification Search
 USPC .......................................................... 424/1.11
 See application file for complete search history.

(56) References Cited

PUBLICATIONS

Thomson et al. (C.R. Chimie 2010, 13, 790-802).*
Reshetnikov (At. Energy 2001, 91, 998-1002).*
Black et al. (J. Alloy Compd. 2001, 315, 36-41).*
Fortier et al. (Dalton Trans. 2009, 39, 352-354).*
Thomson et al. (Nature Chem. 2010, 2, 723-729; Epub Jul. 11, 2010).*

* cited by examiner

*Primary Examiner* — Michael G Hartley
*Assistant Examiner* — Melissa Perreira
(74) *Attorney, Agent, or Firm* — Juliet Ann Jones; Meredith H. Schoefeld; Samuel L. Borkowsky

(57) ABSTRACT

Method for producing terminal uranium nitride complexes comprising providing a suitable starting material comprising uranium; oxidizing the starting material with a suitable oxidant to produce one or more uranium(IV)-azide complexes; and, sufficiently irradiating the uranium(IV)-azide complexes to produce the terminal uranium nitride complexes.

1 Claim, 3 Drawing Sheets

1: R = H, Y = O(2,6-$^i$Pr$_2$C$_6$H$_3$)
2: R = H, Y = NPh$_2$
3: R = H, Y = N(Ph)(SiMe$_3$)
4: R = H, Y = N(SiMe$_3$)$_2$
5: R = Me, Y = N(SiMe$_3$)$_2$

METHOD OF PREPARATION OF URANIUM NITRIDE

REFERENCE TO PRIOR APPLICATION

This application claims the benefit of priority of U.S. Provisional Patent Application 61/385,850, filed Sep. 23, 2010, and incorporated herein in its entirety.

STATEMENT OF FEDERAL RIGHTS

The United States government has rights in this invention pursuant to Contract No. DE-AC52-06NA25396 between the United States Department of Energy and Los Alamos National Security, LLC for the operation of Los Alamos National Laboratory.

FIELD OF THE INVENTION

The present invention relates to methods of preparation of uranium nitrides by means of photolysis of uranium azides.

BACKGROUND OF THE INVENTION

The global energy crisis and anthropogenic global warming have necessitated development of alternate energy sources to curb dependence on fossil fuels. Nuclear energy provides one possible route to alleviate these issues with next generation nuclear reactors and fuels. In this regard, uranium nitride $[U\equiv N]_x$ has arisen as a promising alternative to traditional mixed oxide-fuels, with advantages such as a higher melting point and enhanced thermal conductivity. Unlike the widely studied uranyl ion $[O=U=O]^{2+}$, very little is known about the $U\equiv N$ linkage or its chemical behavior and reactivity. A thorough understanding of the physicochemical properties of the $U\equiv N$ moiety is critical for predicting the long-term behavior of the ceramic nuclear fuel $[U\equiv N]_x$. The properties of extended ceramic materials are challenging to study, and as such molecular model systems are ideal for the controlled study of this bond fragment. Uranium nitrides are rare, and the few known systems have all been generated through oxidation of reduced uranium centers with either dinitrogen or azide sources. The nitride fragments in these complexes either form bridging linkages between uranium centers or coordinate to Lewis acids, namely $B(C_6F_5)_3$. These interactions quench any other potential reactivity of the $U\equiv N$ bond, making the generation of a terminal uranium nitride complex an important goal. A need exists, therefore, for the ability to generate a discrete molecular terminal uranium nitride, which would allow for the study of fundamental reactivity of the isolated $U\equiv N$ fragment and could shed light on the behavior and properties of bulk $[U\equiv N]_x$ under life-cycle conditions from fuel-element formulation to recovery/reprocessing.

By far the most effective route to access nitride species is through photochemical extrusion of $N_2$ from metal azide complexes (M-$N_3$). For example, the photolysis of Fe azide complexes has been successfully utilized to generate terminal Fe nitrides. However, prior to this work, this reaction has not proven successful for analogous uranium complexes.

SUMMARY OF THE INVENTION

The present invention meets the aforementioned need by providing a method of generating a terminal uranium nitride by photolysis of an azide precursor. The $U\equiv N$ linkage of the nitride generated is nucleophilic, and activates a C—H bond to form new C—N and N—H bonds. The present invention demonstrates for the first time that a uranium nitride can be produced through photolysis using energy having wavelengths ranging from approximately 280 nm to 750 nm. The present invention may provide a valuable new means to study of $U\equiv N$ bonds, and provide important insights into the generation and reprocessing of $[U\equiv N]_x$.

The following describes some non-limiting embodiments of the present invention.

According to one embodiment of the present invention, a method for producing terminal uranium nitride complexes is provided comprising providing a suitable starting material comprising uranium; oxidizing the starting material with a suitable oxidant to produce one or more uranium(IV)-azide complexes; and, sufficiently irradiating the uranium(IV)-azide complexes with 280-750 nm light to produce the terminal uranium nitride complexes.

According to yet another embodiment of the present invention, a chemical compound is provided having the following structure:

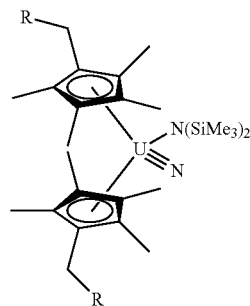

R = H, Me

According to yet another embodiment of the present invention, a chemical compound is provided comprising:

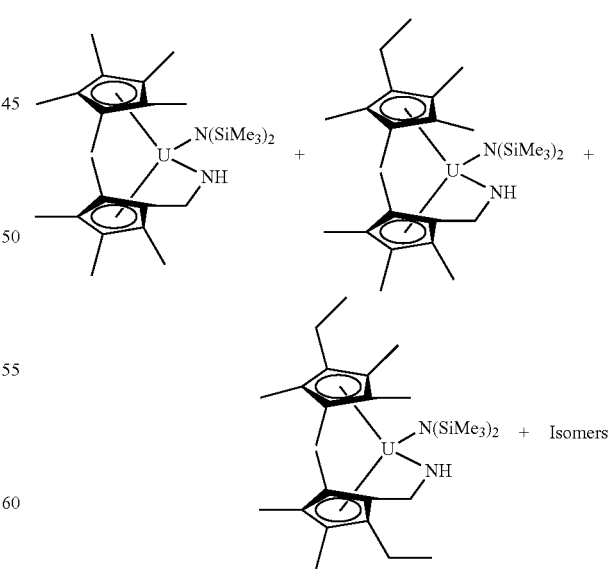

According to yet another embodiment of the present invention, a chemical compound is provided having the following structure:

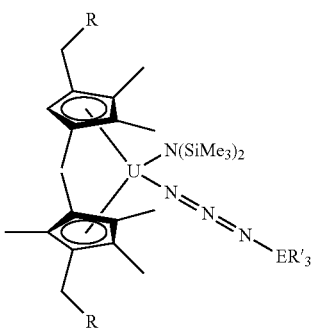

R = H, E = B, R' = C$_6$F$_5$  R = Me, E = B, R' = C$_6$F$_5$  R = Me, E = Al, R' = C$_6$F$_5$  R = H, E = Al, R' = C$_6$F$_5$

DETAILED DESCRIPTION OF THE INVENTION

The present invention describes methods of producing terminal uranium nitrides, which are vital for studying alternative nuclear energy sources. Aspects of the present invention are described in Robert K. Thomson, Thibault Cantat, Brian L. Scott, David E. Morris, Enrique R. Batista and Jaqueline L. Kiplinger, "Uranium Azide Photolysis Results in C—H Bond Activation and Provides Evidence for a Terminal Uranium Nitride." Nature Chemistry, 2010, 2, 723-729 and Robert K. Thomson, Brian L. Scott, David E. Morris and Jaqueline L. Kiplinger, "Synthesis, Structure, Spectroscopy and Redox Energetics of a Series of Uranium(IV) Mixed-Ligand Metallocene Complexes," Comptes Rendus Chimie, 2010, 13, 790-802, incorporated herein by reference in their entirety.

Figure 1:
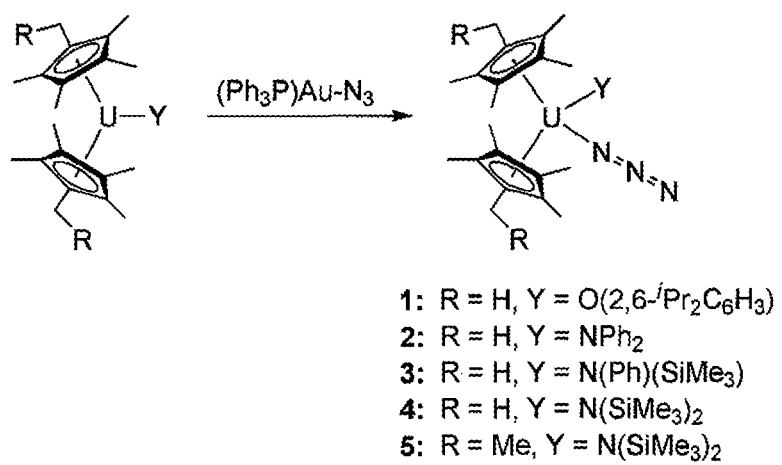
FIG. 1 depicts various starting materials and end products of the method of the present invention to generate uranium (IV)azide complexes.

The method of the present invention comprises providing a suitable starting material comprising uranium, and, oxidizing said starting material with a suitable oxidant to produce uranium(IV)-azide complexes (FIG. 1, structures 4 and 5). The resultant uranium (IV)-azide complexes are then subjected to irradiation with 280-750 nm light, which results in loss of dinitrogen and generation of terminal uranium nitride complexes. In an alternative embodiment, the uranium(IV)azide complexes may be reacted with a group 13 compound to produce azidoborate and azidoaluminate complexes.

Suitable uranium-containing starting materials are described in Robert K. Thomson, Christopher R. Graves, Brian L. Scott and Jaqueline L. Kiplinger, "Noble Reactions for the Actinides: Safe Gold-Based Access to Organouranium and Azido Complexes," European Journal of Inorganic Chemistry, 2009, 1451-1455; Robert K. Thomson, Brian L. Scott, David E. Morris and Jaqueline L. Kiplinger, "Synthesis, Structure, Spectroscopy and Redox Energetics of a Series of Uranium(IV) Mixed-Ligand Metallocene Complexes," Comptes Rendus Chimie, 2010, 13, 790-802; Christopher R. Graves, Brian L. Scott, David E. Morris and Jaqueline L. Kiplinger, "Tetravalent and Pentavalent Uranium Acetylide Complexes Prepared by Oxidative Functionalization with CuC≡CPh," Organometallics, 2008, 27, 3335-3337; Juan M. Manriquez, Paul J. Fagan, Tobin J. Marks, Sara H. Vollmer, Cynthia Secaur Day and Victor W. Day, "Pentamethylcyclopentadienyl Organoactinides. Trivalent Uranium Organometallic Chemistry and the Unusual Structure of Bis(pentamethylcyclopentadienyl)uranium Monochloride." Journal of the American Chemical Society, 1979, 101, 5075-5078; Eric J. Schelter, Ruilian Wu, Brian L. Scott, Joe D. Thompson, David E. Morris and Jaqueline L. Kiplinger, "Mixed Valency in a Uranium Multimetallic Complex," Angewandte Chemie International Edition, 2008, 47, 2993-2996; David S. J. Arney and Carol J. Burns, "Synthesis and Properties of High-Valent Organouranium Complexes Containing Terminal Organoimido and Oxo Functional Groups. A New Class of Organo-f-Element Complexes," Journal of the American Chemical Society, 1995, 117, 9448-9460; David S. J. Arney and Carol J. Burns, "Synthesis and Structure of High-Valent Organouranium Complexes Containing Terminal Monooxo Functional Groups," Journal of the American Chemical Society, 1993, 115, 9840-9841; incorporated herein by reference in their entirety, and include the uranium(III) complexes $(C_5Me_5)_2U(O-2,6-^iPr_2-C_6H_3)(THF)$, $(C_5Me_5)_2U(NPh_2)(THF)$, $(C_5Me_5)_2U[N(Ph)(SiMe_3)](THF)$, $(C_5Me_5)_2U[N(SiMe_3)_2]$, $(C_5Me_4Et)_2U[N(SiMe_3)_2](THF)$ and the imido-uranium(IV) complexes $(C_5Me_5)_2U(=N-2,4,6-^tBu_3-C_6H_2)$ and $(C_5Me_5)_2U(=N-2,6-^iPr_2-C_6H_3)(THF)$. Examples of suitable oxidants for the uranium-containing starting material include $(Ph_3P)Au$—X (X=N$_3$, CH$_3$, CF$_3$, C≡-(4-C$_6$H$_4$—CH$_3$)), AgNCO, and CuX or CuX$_2$ (X=I, Br, Cl, F, OSO$_2$CF$_3$, SPh, Ca≡CPh).

The uranium(IV)-azide complexes resulting from the oxidation of the uranium-containing starting material include structures 1, 2, 3, 4 and 5 depicted in FIG. 1. The uranium (IV)-azide complexes are then irradiated with energy, which results in one or more terminal uranium nitride complexes. The energy may encompass a wide range of the electromagnetic spectrum, and may be in the ultraviolet, visible or infrared range of the spectrum. In one embodiment, the energy is in the ultraviolet and visible range, and has a wavelength of from about 280 nm to about 750 nm. In one embodiment, the irradiated uranium(IV)-azide complexes are structures 4 and 5 depicted in FIG. 1. In one embodiment, the terminal uranium nitride complexes have the following structure (depicted in FIG. 2):

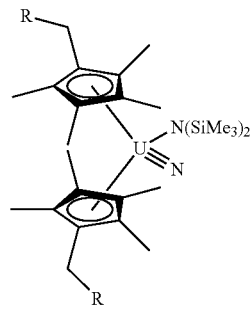

R = H, Me

In one embodiment, the uranium(IV)-azide complexes may be reacted with a group 13 alkyl or aryl compound to produce one or more azidoborate complexes. Herein, "group 13 compound" is understood to include a chemical compound comprising one or more elements from group 13 (IUPAC nomenclature) of the periodic table. In one embodiment, the group 13 compound comprises boron and/or aluminum, and alternatively, the group 13 compound is $B(C_6F_5)_3$, $AlMe_3$, or $Al(C_6F_5)_3$. Non-limiting examples of azidoborate and azidoaluminate complexes include structures 10-11 and 12-13, respectively, depicted in FIG. 3.

Figure 2:
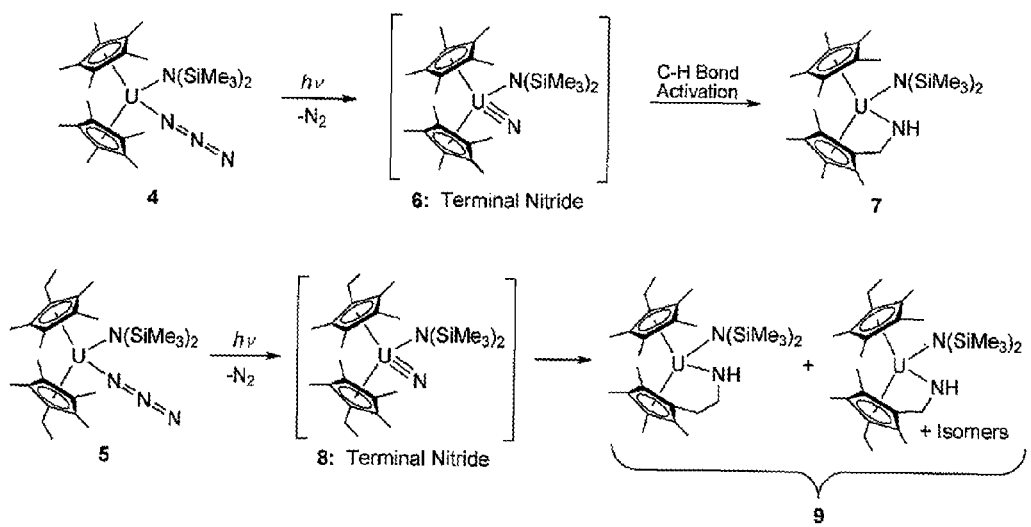
FIG. 2 depicts various reactions employing the method of the present invention to photochemically generate terminal uranium nitrides and the reactivity thereof.

The terminal uranium nitride complex may in turn undergo C—H bond activation to form a variety of structures, one of which is structure 7 in FIG. 2:

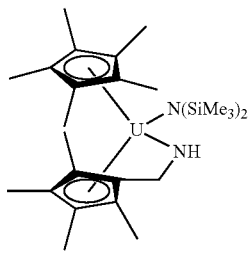

EXAMPLES

General Experimental Procedures

Unless otherwise specified, all reactions and manipulations were performed under a dry oxygen-free atmosphere of dinitrogen in either a Vacuum Atmospheres NEXUS model drybox equipped with a 40CFM Dual Purifier NI-Train, or by using standard Schlenk techniques. Glassware was dried in an oven at 150° C. overnight prior to use. All NMR spectra were collected using a Bruker Avance 300 MHz NMR spectrometer. Chemical shifts for $^1$H NMR spectra are reported in parts per million (ppm), and were referenced to residual proton references calibrated against external tetramethylsilane ($SiMe_4$). $^{19}$F NMR spectra were calibrated against external trifluoromethanesulfonic acid ($CF_3SO_3H$). Infrared spectra were collected on a Nicolet Avatar 370 DTGS spectrophotometer. Mass spectrometric (MS) analyses were performed at the University of California, Berkeley Mass Spectrometry Facility, using a VG Prospec (EI) mass spectrometer. Elemental analyses were performed at either the University of California, Berkeley Microanalytical Facility, on a Perkin-Elmer Series II 2400 CHNS analyzer, or at Columbia Analytical Services, or Midwest Microlab LLC. X-ray data were collected using a Bruker APEX2 diffractometer. Structural solution and refinement was achieved using the SHELXL program suite, i.e., Bruker, APEX2 1.08, APEX2 Data Collection Software; Bruker Analytical X-ray Systems: Madison, Wis., 2003; Bruker, SAINT+7.06, Integration Software; Bruker Analytical X-ray Systems: Madison, Wis., 2001; Sheldrick, G. M. SADABS 2.03, Program for Adsorption Correction; University of Göttingen: Göttingen, Germany, 2001; Sheldrick, G. M. SHELXS-97 and SHELXL-97, Structure Solution and Refinement Package; University of Göttingen: Göttingen, Germany, 1997; Bruker, SHELXTL 6.10, Molecular Graphics and Publication Software Package; Bruker Analytical X-ray Systems: Madison, Wis., 2000. Details regarding data collection are provided in the CIF files which can be found at DOI: 10.1038/NCHEM.705

Except where otherwise noted, reagents were purchased from commercial suppliers and used without further purification. Benzene-d$_6$ (Aldrich, anhydrous), toluene-4 (Aldrich, anhydrous), and tetrahydrofuran-4 (Cambridge Isotope Laboratories) were purified by storage over 4 Å molecular sieves under $N_2$ prior to use. Celite (Aldrich), alumina (Aldrich, Brockman I), and 4 Å molecular sieves (Aldrich) were dried under dynamic vacuum at 250° C. for 48 h prior to use. All solvents (Aldrich) were purchased anhydrous and dried over KH for 24 h, passed through a column of activated alumina, and stored over activated 4 Å molecular sieves prior to use. The following compounds were prepared according to literature procedures: $(C_5Me_5)_2U(O-2,6-^iPr_2C_6H_3)(N_3)$, $(C_5Me_5)_2U(NPh_2)(THF)$, $(C_5Me_5)_2U[N(Ph)(SiMe_3)]$ (THF), $(C_5Me_5)_2U[N(SiMe_3)_2]$, and $(C_5Me_4Et)_2U[N(SiMe_3)_2](THF)$. Caution: Depleted uranium (primary isotope $^{238}$U) is a weak alpha-emitter (4.197 MeV) with a half-life of $4.47 \times 10^9$ years; manipulations and reactions should be carried out in monitored fume hoods or in an inert atmosphere drybox in a radiation laboratory equipped with alpha- and beta-counting equipment.

Synthesis

Synthesis of $(Ph_3P)Au—N_3$

A 125-mL side-arm flask (wrapped with Al foil to exclude light) equipped with a stir bar was charged with $(Ph_3P)Au—O^tBu$ (2.12 g, 3.99 mmol, 1 equiv.) and tetrahydrofuran (50 mL) at room temperature. To this stirring solution was added a tetrahydrofuran (10 mL) solution of $Me_3SiN_3$ (2.30 g, 19.9 mmol, ~5 equiv.). After 5 hours the reaction mixture was filtered through a Celite-padded coarse-porosity filter, the filtrate collected and the volatiles removed under reduced pressure to give an off-white residue. Note: Allowing this reaction to proceed for longer periods of time generally results in low yields through decomposition. The off-white residue was washed with hexanes (35 mL), collected by filtration and dried under reduced pressure to give $(Ph_3P)Au—N_3$ as a white solid (1.85 g, 3.69 mmol, 93%). This complex is indefinitely stable if stored in a dark freezer at −30° C. $^1$H NMR (300 MHz, benzene-d$_6$, 25° C.): δ=6.84 (m, 6H, et-Ar—H), 6.98 (m, 9H, m/p-Ar—H). $^{31}$P NMR ($C_6D_6$, 121 MHz, 298 K): δ 30.4. IR (Nujol, cm$^{-1}$): 2052.7.

Synthesis of $(C_5Me_5)_2U(NPh_2)(N_3)$, 2 (FIG. 1)

A 125-mL side-arm flask equipped with a stir bar was charged with $(C_5Me_5)_2U(NPh_2)(THF)$ (0.224 g, 0.299 mmol) and toluene (30 mL). To this green solution was added $(Ph_3P)Au—N_3$ (0.150 g, 0.299 mmol). The solution immediately turned dark red in color and was stirred at room temperature for 15 h. The solution was then filtered through a Celite-padded medium-porosity fritted-filter and the Celite plug was washed with toluene (5 mL) until the washings were colorless. The filtrate was collected and volatiles were removed under reduced pressure to give a tarry red residue, which was dissolved in hexane (30 mL) and filtered through a Celite-padded medium-porosity fritted-filter. The Celite plug was washed with hexane (10 mL) until the washings were colorless. The resulting red filtrate was collected and volatiles were removed under reduced pressure to give $(C_5Me_5)_2U(NPh_2)(N_3)$ as a dark red solid (0.175 g, 0.242 mmol, 81% yield). $^1$H NMR (300 MHz, benzene-d$_6$, 25° C.): δ=−18.57 (s, 2H, Ar—H), −5.36 (t, J=7 Hz, 1H, Ar—H), −4.65 (s, 2H, Ar—H), −4.15 (t, J=7 Hz, Ar—H), 6.82 (d, J=9 Hz, 1H, Ar—H), 7.01 (s, 2H, Ar—H), 7.37 (s, 1H, Ar—H), 10.69 (s, 30H, $C_5Me_5$). IR (Nujol, cm$^{-1}$): ν 2087(s) ($N_3$ asymmetric stretch). MS (EL 70 eV): m/z 718 [M$^+$]. Anal. Calcd. for $C_{32}H_{40}N_4U$ (mol. wt. 718.73): C, 53.48; H, 5.61; N, 7.80. Found: C, 53.29; H, 5.50; N, 7.59.

Synthesis of $(C_5Me_5)_2U[N(Ph)(SiMe_3)](N_3)$, 3 (FIG. 1)

A 125-mL side-arm flask equipped with a magnetic stir bar was charged with $(C_5Me_5)_2U[N(Ph)(SiMe_3)](THF)$ (0.280 g, 0.376 mmol) and toluene (50 mL). To this stirred green solution was added $(Ph_3P)Au-N_3$ (0.181 g, 0.376 mmol) as a solid, resulting in an immediate color change to dark red. The resulting solution was stirred at room temperature. After 15 h, the reaction mixture was filtered through a Celite-padded coarse-porosity fitted filter, and the Celite plug was washed with toluene until the washings went colorless. The filtrate was collected and the volatiles were removed under reduced pressure. The resulting red solid was extracted into hexanes and filtered through a Celite-padded coarse-porosity fitted filter, and the Celite plug was washed with hexanes until the washings went colorless. The red colored filtrate was collected and the volatiles were removed under reduced pressure to give $(C_5Me_5)_2U[N(Ph)(SiMe_3)](N_3)$ as a dark red solid (0.215 g, 0.301 mmol, 80%). $^1$H NMR (300 MHz, benzene-$d_6$, 25° C.): δ=−10.12 (s, 2H, o/m-Ar), −5.82 (t, J=7 Hz, 1H, p-Ar), 0.30 (s, 2H, o/m-Ar), 1.31 (s, 9H, SiMe$_3$), 8.45 (s, 30H, $C_5Me_5$). IR (Nujol, cm$^{-1}$): ν 2087 (s) (N$_3$ asymmetric stretch). Anal. Calcd. for $C_{29}H_{44}N_4SiU$ (mol. wt. 714.80 gmol$^{-1}$): C, 48.73; H, 6.20; N, 7.84. Found: C, 48.50; H, 6.32; N, 7.75.

Synthesis of $(C_5Me_5)_2U[N(SiMe_3)_2](N_3)$, 4 (FIG. 1)

A 125-mL side-arm flask equipped with a stir bar was charged with $(C_5Me_5)_2U[N(SiMe_3)_2]$ (0.875 g, 1.31 mmol) and toluene (50 mL). To this green solution was added $(Ph_3P)Au-N_3$ (0.656 g, 1.31 mmol). The solution immediately turned dark red in color and was stirred at room temperature. After 15 h, the solution was filtered through a Celite-padded coarse-porosity fitted-filter and the Celite plug was washed with toluene (10 mL) until the washings were colorless. The filtrate was collected and volatiles were removed under reduced pressure to give a red residue, which was dissolved in hexanes (30 mL) and filtered through a Celite-padded coarse-porosity fritted-filter. The Celite plug was washed with hexane (10 mL) until the washings were colorless. The resulting red filtrate was collected and volatiles were removed under reduced pressure to give $(C_5Me_5)_2U[N(SiMe_3)_2](N_3)$ as dark red crystals (0.825 g, 1.17 mmol, 89% yield). $^1$H NMR (300 MHz, benzene-$d_6$, 25° C.): δ=−101.60 (s, 3H, SiCH$_3$), 3.31 (s, 6H, Si(CH$_3$)$_2$), 4.79 (s, 9H, Si(CH$_3$)$_3$), 8.66 (s, 30H, $C_5Me_5$). IR (Nujol, cm$^{-1}$): ν 2090(s) (N$_3$ asymmetric stretch). MS (EI, 70 eV): m/z 710 [M$^+$]. Anal. Calcd. for $C_{26}H_{48}N_4Si_2U$ (mol. wt. 710.89 gmol$^{-1}$): C, 43.93; H, 6.81; N, 7.88. Found: C, 44.22; 1-1, 6.69; N, 7.87.

Synthesis of $(C_5Me_4Et)_2U[N(SiMe_3)_2](N_3)$, 5 (FIG. 1)

A 125-mL side-arm flask equipped with a stir bar was charged with $(C_5Me_4Et)_2U[N(SiMe_3)_2]$ (0.250 g, 0.359 mmol) and toluene (35 mL). To this green-brown solution was added $(Ph_3P)Au-N_3$ (0.180 g, 0.359 mmol). The solution immediately turned dark red in color and was stirred at room temperature for 15 h. The solution was then filtered through a Celite-padded medium-porosity fitted-filter and the Celite plug was washed with toluene (10 mL) until the washings were colorless. The filtrate was collected and volatiles were removed under reduced pressure to give a red residue, which was dissolved in pentane (30 mL) and filtered through a Celite-padded medium-porosity fritted-filter. The Celite plug was washed with pentane (10 mL) until the washings were colorless. The resulting red filtrate was collected and volatiles were removed under reduced pressure to give $(C_5Me_4Et)_2U[N(SiMe_3)_2](N_3)$ as dark red crystals (0.220 g, 0.298 mmol, 83% yield). $^1$H NMR (300 MHz, benzene-$d_6$, 25° C.): δ=−102.32 (s, 314, SiCH$_3$), 0.63 (q, J=6 Hz, 2H, $C_5Me_4CH_2CH_3$), 0.79 (q, J=7 Hz, 2H, $C_5Me_4CH_2CH_3$), 3.05 (s, 6H, Si(CH$_3$)$_2$), 4.49 (s, 9H, Si(CH$_3$)$_3$), 7.78 (s, 6H, o-$C_5Me_4Et$), 8.48 (t, J=7 Hz, 6H, $C_5Me_4CH_2CH_3$), 9.08 (s, 12H, m-$C_5Me_4Et$), 9.34 (s, 6H, o-$C_5Me_4Et$). 1R (Nujol, cm$^{-1}$): ν 2089(s) (N$_3$ asymmetric stretch). Anal. Calcd. for $C_{28}H_{52}N_4Si_2U \cdot 0.5(C_5H_{12})$ (mol. wt. 775.02 gmol$^{-1}$): C, 47.27; H, 7.54; N, 7.23. Found: C, 47.05; H, 7.18; N, 7.37.

Synthesis of $(C_5Me_5)(C_5Me_4CH_2NH)U[N(SiMe_3)_2]$, 7 (FIG. 2)

A 20-mL thick-walled Schlenk tube equipped with a Teflon valve and a stir bar was charged with $(C_5Me_5)_2U[N(SiMe_3)_2](N_3)$ (0.250 g, 0.352 mmol) and toluene (15 mL). The Teflon valve was wrapped with aluminum foil to prevent degradation. The reaction vessel was irradiated at room temperature using a water-cooled Hanovia 450 W medium-pressure Hg lamp filtered through a Pyrex cell at a distance of ca. 5 cm. After 80 h, the volatiles were removed from the reaction mixture under reduced pressure to yield a red-brown solid, which was dissolved in hexanes (20 mL) and filtered through a Celite-padded coarse-porosity fritted-filter. The Celite plug was washed with hexane (5 mL) until the washings went colorless. The filtrate was collected and the volatiles were removed under reduced pressure to give $(C_5Me_5)(C_5Me_aCH_2NH)U[N(SiMe_3)_2]$ as a red-brown solid (0.200 g, 0.299 mmol, 85% yield). $^1$H NMR (300 MHz, benzene-$d_6$, 25° C.): δ=−111.63 (s, 1H, NH), −27.08 (s, 3H, CH$_3$), −8.61 (s, 9H, Si(CH$_3$)$_3$), −2.57 (s, 3H, CH$_3$), 1.04 (s, 3H, CH$_3$), 1.19 (s, 18H, $C_5Me_5+CH_3$), 11.49 (s, 3H, CH$_3$), 17.18 (s, 3H, CH$_3$), 23.06 (s, 3H, CH$_3$), 41.36 (d, J=11 Hz, 1H, CH$_2$), 52.36 (d, J=11 Hz, 1H, CH$_2$). IR (Nujol, cm$^{-1}$): ν 3308(w) (NH stretch). MS (EI, 70 eV): m/z 682 [M$^+$]. Anal. Calcd. for $C_{26}H_{48}N_2Si_2U$ (mol. wt. 682.88 gmol$^{-1}$): C, 45.73; H, 7.08; N, 4.10. Found: C, 45.17; H, 7.03; N, 4.32.

Synthesis of $(C_5Me_4Et)(C_5Me_4CH_2CH_2NE)U[N(SiMe_3)_2]$ and Isomers of $(C_5Me_4Et)(C_5Me_3EtCH_2NH)U[N(SiMe_3)_2]$, 9 (FIG. 2)

A 20-mL scintillation vial equipped with a stir bar was charged with $(C_5Me_4Et)_2U[N(SiMe_3)_2](N_3)$ (0.025 g, 0.034 mmol) and benzene-$d_6$ (1.5 mL). The deep red solution was transferred to a J-Young NMR tube, which was capped with a Teflon valve. The valve was wrapped with aluminum foil to prevent degradation. The reaction vessel was irradiated at room temperature using a water-cooled Hanovia 450 W medium-pressure Hg lamp filtered through a Pyrex cell at a distance of ca. 5 cm for 48 h. The reaction mixture was analyzed by $^1$H NMR spectroscopy, which showed complete consumption of the starting material and formation of a mixture of $(C_5Me_4Et)(C_5Me_4CH_2CH_2NH)U[N(SiMe_3)_2]$ and all possible isomers of $(C_5Me_4Et)(C_5Me_3EtCH_2NH)U[N(SiMe_3)_2]$. $^1$H NMR (300 MHz, benzene-$d_4$, 25° C.): Diagnostic signals for the U—NH and $(C_5R_4(CH_2)_n)$ (R$_4$=Me$_4$, n=2; R$_4$=Me$_3$Et, n=1) protons for the different isomers of $(C_5Me_4Et)(C_5R_4(CH_2)_n)U[N(SiMe_3)_2]$ (R$_4$=Me$_4$, n=2; R$_4$=Me$_3$Et, n=1): δ=−110.32 (s, NH), −110.18 (s, NH), −109.34 (s, NH), −107.59 (s, NH), −107.31 (s, NH), −8.85 (t, J=56 Hz, $C_5Me_4CH_2CH_2$), 22.61 (t, J=68 Hz, $C_5Me_4CH_2CH_2$), 41.30 (d, J=11 Hz, $C_5Me_3EtCH_2NH$), 41.44 (d, J=10 Hz, C$_5$Me$_3$EtCH$_2$NH), 41.63 (d, J=11 Hz, C$_5$Me$_3$EtCH$_2$NH), 41.93 (m, C$_5$Me$_3$EtCHCH$_3$NH), 42.47 (d, J=11 Hz, C$_5$Me$_3$EtCH$_2$NH), 52.12 (d, J=11 Hz, C$_5$Me$_3$EtCH$_2$NH), 53.01 (d, J=10 Hz, C$_5$Me$_3$EtCH$_2$NH), 54.33 (d, J=11 Hz, C$_5$Me$_3$EtCH$_2$NH), 54.82 (d, J=10 Hz, C$_5$Me$_3$EtCH$_2$NH).

Figure 3:
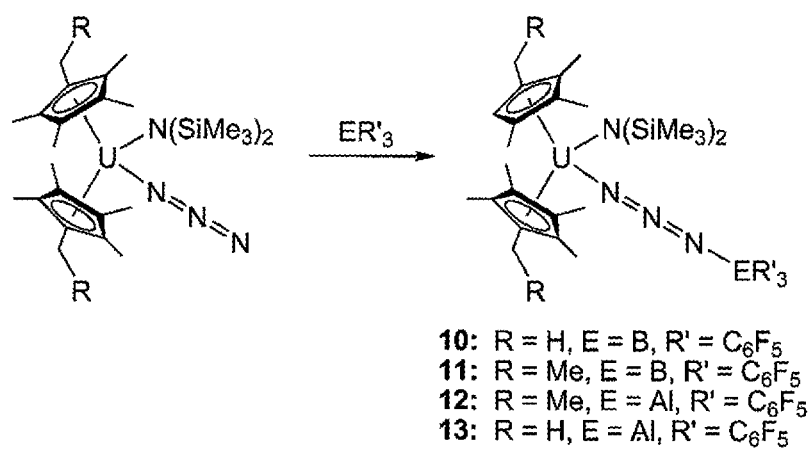
FIG. 3 depicts the various starting materials and end products of the method of the present invention to generate uranium(IV)azidoborate and azidoaluminate complexes.

Synthesis of (C$_5$Me$_5$)$_2$U[N(SiMe$_3$)$_2$](μ-η$^1$:η$^1$-N$_3$)[B(C$_6$F$_5$)$_3$], 10 (FIG. 3)

A 20-mL scintillation vial was charged with a stir bar, (C$_5$Me$_5$)$_2$U[N(SiMe$_3$)$_2$](N$_3$) (0.198 g, 0.279 mmol) and toluene (10 mL). To the resulting solution a toluene (5 mL) solution of B(C$_6$F$_5$)$_3$ (0.143 g, 0.279 mmol) was added by pipette. The dark red solution was stirred at room temperature for 15 h and filtered through a Celite-padded medium-porosity fitted-filter. The Celite plug was washed with toluene (5 mL) until the washings were colorless. The filtrate was collected and the volatiles were removed under reduced pressure to give a tacky red residue. This residue was triturated with hexamethyldisiloxane (5 mL) and collected on a fine porosity flitted-filter and dried under reduced pressure to give (C$_5$Me$_5$)$_2$U[N(SiMe$_3$)$_2$](μ-η$^1$:η$^1$-N$_3$)[B(C$_6$—F$_5$)$_3$] as a red solid (0.250 g, 0.204 mmol, 73% yield). $^1$H NMR (300 MHz, benzene-d$_6$, 25° C.): δ=−116.22 (s, 3H, SiCH$_3$), 6.66 (s, 6H, Si(CH$_3$)$_2$), 7.08 (s, 9H, Si(CH$_3$)$_3$), 10.1.8 (s, 30H, C$_5$Me$_5$). $^{19}$F NMR (282 MHz, benzene-d$_6$, 25° C.): −147.85 (d, J=23 Hz, o-Ar—F), −160.08 (br, p-Ar—F), −167.95 (br, m-Ar—F). IR (Nujol, cm$^{-1}$): ν 2178(s) (N$_3$ asymmetric stretch).

Synthesis of (C$_5$Me$_4$Et)$_2$U[N(SiMe$_3$)$_2$](μ-η$^1$:η$^1$-N$_3$)[B(C$_6$F$_5$)$_3$], 11 (FIG. 3)

A 20-mL scintillation vial equipped with a stir bar was charged with (C$_5$Me$_4$Et)$_2$U[N(SiMe$_3$)$_2$](N$_3$) (0.100 g, 0.135 mmol) and toluene-4 (3 mL). To this red solution was added B(C$_6$F$_5$)$_3$ (0.069 g, 0.135 mmol). The solution immediately became a dark red color and was stirred at room temperature. After 15 h, the solution was filtered through a Celite-padded coarse-porosity fritted-filter and the Celite plug was washed with benzene (5 mL) until the washings were colorless. The filtrate was collected and volatiles were removed under reduced pressure to give a red residue, which was triturated with pentane (20 mL) and collected on a medium-porosity fritted-filter (0.100 g). The resulting red filtrate was collected and volatiles were removed under reduced pressure to yield a dark red solid (0.035 g). $^1$H NMR spectroscopy confirmed that both products are (C$_5$Me$_4$Et)$_2$U[N(SiMe$_3$)$_2$](μ-η$^1$:η$^1$-N$_3$)[B(C$_6$F$_5$)$_3$] (0.135 g, 0.108 mmol, 80% yield). $^1$H NMR (300 MHz, toluene-d$_5$, 25° C.): δ=−116.40 (s, 3H, SiCH$_3$), −0.51 (m, 2H, C$_5$Me$_4$CH$_2$CH$_3$), 0.78 (m, 2H, C$_5$Me$_4$CH$_2$CH$_3$), 6.45 (s, 6H, Si(CH$_3$)$_2$), 6.84 (s, 9H, Si(CH$_3$)$_3$), 7.07 (t, J=7 Hz, 6H, C$_5$Me$_4$CH$_2$CH$_3$), 9.04 (s, 6H, C$_5$Me$_4$Et), 10.47 (s, 6H, C$_5$Me$_4$Et), 10.63 (s, 6H, C$_5$Me$_4$Et), 12.35 (s, 6H, C$_5$Me$_4$Et). $^{19}$F NMR (282 MHz, toluene-d$_8$, 25° C.): δ=−147.92 (d, J=20 Hz, o-Ar—F), −160.30 (t, J=20 Hz, p-Ar—F), −168.12 (m, m-Ar—F). IR (Nujol, cm$^{-1}$): ν 2180(s) (N$_3$ asymmetric stretch). Anal Calcd for C$_{46}$H$_{52}$BF$_{15}$N$_4$Si$_2$U (mol. wt. 1250.93 gmol$^{-1}$): C, 44.17; H, 4.19; N, 4.48. Found: C, 43.93; H, 4.14; N, 4.24.

Synthesis of (C$_5$Me$_4$Et)$_2$U[N(SiMe$_3$)$_2$](μ-η$^1$:η$^1$-N$_3$)[AlMe$_3$], 12 (FIG. 3)

A 125-mL side-arm flask equipped with a stir bar was charged with (C$_5$Me$_4$Et)$_2$U[N(SiMe$_3$)$_2$](N$_3$) (0.250 g, 0.338 mmol) and toluene (20 mL). To this red solution was added AlMe$_3$ (205 μL, 2.0 M/toluene, 0.410 mmol) using a microsyringe. The solution immediately became a dark red color and was stirred at room temperature for 18 h. The resulting solution was filtered through a Celite-padded coarse-porosity fritted-filter and the Celite plug was washed with toluene (5 mL) until the washings were colorless. The filtrate was collected and volatiles were removed under reduced pressure to give a red crystalline material. This red material was dissolved in hexane (40 mL) and filtered through a Celite-padded coarse-porosity fritted-filter, and the Celite plug was washed with hexane (5 mL) until the washings went colorless. The filtrate was collected and the volatiles were removed under reduced pressure to give (C$_5$Me$_4$Et)$_2$U[N(SiMe$_3$)$_2$](μ-η$^1$:η$^1$-N$_3$)[AlMe$_3$] as a dark red solid (0.220 g, 0.271 mmol, 80% yield). $^1$H NMR spectroscopy of this material indicates the formation of a new azide adduct, but the AlMe$_3$ is not visible by $^1$H NMR. This material was redissolved in hexane and crystallized at −35° C. in the presence of excess AlMe$_3$, generating single crystals for X-ray diffraction. $^1$H NMR (300 MHz, C$_6$D$_6$, 25° C.): δ=−115.73 (s, 3H, SiCH$_3$), −9.02 (s, 9H, Al(CH$_3$)$_3$), 0.063 (d, J=6 Hz, 2H, C$_5$Me$_4$CH$_2$CH$_3$), 0.056 (d, J=6 Hz, 2H, C$_5$Me$_4$CH$_2$CH$_3$), 5.84 (s, 6H, Si(CH$_3$)$_2$), 6.56 (s, 9H, Si(CH$_3$)$_3$), 7.47 (m, 6H, C$_5$Me$_4$CH$_2$CH$_3$), 8.74 (s, 6H, C$_5$Me$_4$Et), 9.87 (s, 6H, C$_5$Me$_4$Et), 10.24 (s, 6H, C$_5$Me$_4$Et), 12.29 (s, 6H, C$_5$Me$_4$Et). IR (Nujol, cm$^{-1}$): ν 2150 (s) (N$_3$ asymmetric stretch). Anal Calculated for C$_{31}$H$_{61}$AlN$_4$Si$_2$U (mol. wt. 811.03 gmol$^{-1}$): C, 45.91; H, 7.58; N, 6.91. Found: C, 46.00; H, 7.70; N, 7.00.

Synthesis of (C$_5$Me$_5$)$_2$U[N(SiMe$_3$)$_2$](μ-η$^1$:η$^1$-N$_3$)[Al(C$_6$F$_5$)$_3$], 13 (FIG. 3)

A 20-mL scintillation vial equipped with a stir bar was charged with (C$_5$Me$_5$)$_2$U[N(SiMe$_3$)$_2$](N$_3$) (0.249 g, 0.350 mmol) and toluene (8 mL). To this red solution was added (C$_7$—H$_8$)Al(C$_6$F$_5$)$_3$ (0.217 g, 0.350 mmol) as a solid. The solution immediately became a dark red color and was stirred at room temperature for 4 h. The resulting solution was filtered through a Celite-padded coarse-porosity flitted filter and the Celite plug was washed with toluene (5 mL) until the washings went colorless. The filtrate was collected and the volatiles were removed under reduced pressure to give a red solid. The solid was washed with hexane (10 mL) and collected on a medium-porosity fitted filter and dried under reduced pressure to give (C$_5$Me$_5$)$_2$U[N(SiMe$_3$)$_2$](μ-η$^1$:η$^1$-N$_3$)[Al(C$_6$F$_5$)$_3$] as a dark red solid (0.340 g, 0.274 mmol, 78% yield). $^1$H NMR (300 MHz, C$_6$D$_6$, 25° C.): δ=−112.80 (s, 3H, SiCH$_3$), 5.66 (s, 6H, Si(CH$_3$)$_2$), 6.45 (s, 9H, Si(CH$_3$)$_3$), 9.37 (s, 30H, C$_5$Me$_5$). $^{19}$F NMR (282 MHz, C$_6$D$_6$, 25° C.): δ=−133.93 (br d, o-Ar—F), −156.17 (t, J=21 Hz, p-Ar—F), −165.76 (m, m-Ar—F). Infrared (Nujol, cm$^-$): ν 2180 (s) (N$_3$ asymmetric stretch). Anal Calcd for C$_{44}$H$_{48}$AlF$_{15}$N$_4$Si$_2$U (mol. wt. 1239.05 gmol$^{-1}$): C, 42.65; H, 3.91; N, 4.52. Found: C, 42.75; H, 4.00; N, 4.42.

In all embodiments of the present invention, all numerical amounts are understood to be modified by the word "about" unless otherwise specifically indicated. All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

Whereas particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A chemical compound having the following structure:
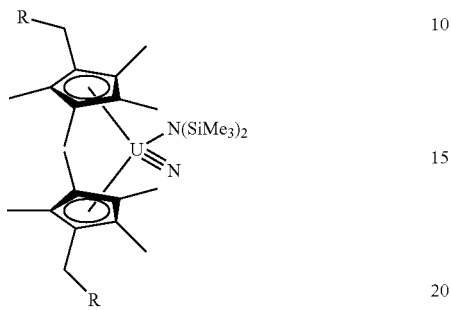
R = H, Me
wherein R is hydrogen or methyl.
* * * * *